(12) United States Patent
Keller

(10) Patent No.: US 7,722,673 B2
(45) Date of Patent: May 25, 2010

(54) INTERVERTEBRAL DISC PROSTHESIS

(75) Inventor: Arnold Keller, Kayhude (DE)

(73) Assignee: Cervitech, Inc., San Diego, CA (US)

( * ) Notice: Subject to any disclaimer, the term of this patent is extended or adjusted under 35 U.S.C. 154(b) by 0 days.

(21) Appl. No.: 10/623,803

(22) Filed: Jul. 22, 2003

(65) Prior Publication Data

US 2005/0021143 A1    Jan. 27, 2005

(51) Int. Cl.
*A61F 2/44* (2006.01)
(52) U.S. Cl. .................................................. 623/17.11
(58) Field of Classification Search ............... 606/60, 606/61; 623/11.11, 16.11, 17.11–17.16
See application file for complete search history.

(56) References Cited

U.S. PATENT DOCUMENTS

| | | | |
|---|---|---|---|
| 4,743,261 A * | 5/1988 | Epinette | 623/20.32 |
| 4,759,766 A * | 7/1988 | Buettner-Janz et al. | 623/17.15 |
| 5,405,396 A * | 4/1995 | Heldreth et al. | 623/20.32 |
| 5,425,773 A * | 6/1995 | Boyd et al. | 623/17.15 |
| 6,468,311 B2 * | 10/2002 | Boyd et al. | 623/17.16 |
| 2004/0117022 A1 * | 6/2004 | Marnay et al. | 623/17.16 |

FOREIGN PATENT DOCUMENTS

| | | | |
|---|---|---|---|
| EP | 0636352 A2 | * | 2/1995 |
| FR | 2 632 516 | | 6/1988 |
| FR | 2 718 635 | | 4/1994 |
| FR | 2 780 635 | | 7/1998 |
| WO | WO02089701 | * | 11/2002 |

OTHER PUBLICATIONS

Translation of Olivier Caenen, et al. (FR 2,718,635).*
European Search Report dated Dec. 4, 2003.
Letter dated Jan. 23, 2004, from client regarding European Search Report.

* cited by examiner

*Primary Examiner*—Anu Ramana
(74) *Attorney, Agent, or Firm*—Morrison & Foerster LLP

(57) ABSTRACT

An intervertebral disc prosthesis has two cover plates and a prosthesis core which is connected to one of the cover plates by of connection profiles on one of the cover plates which are undercut in a complementary manner and include at least one pair of profile sections which are symmetrical with respect to the AP (anterior-posterior) direction of the prosthesis in its implanted position and are arranged at an angle to one another.

2 Claims, 1 Drawing Sheet

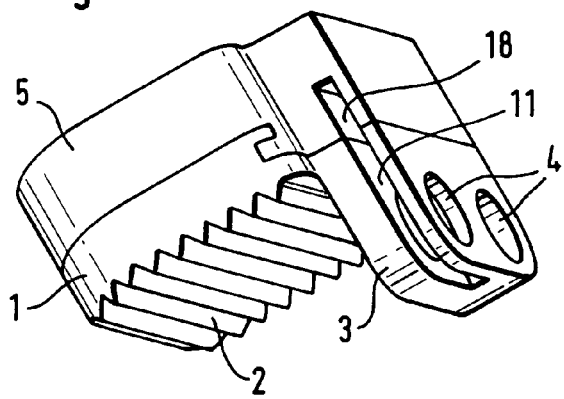
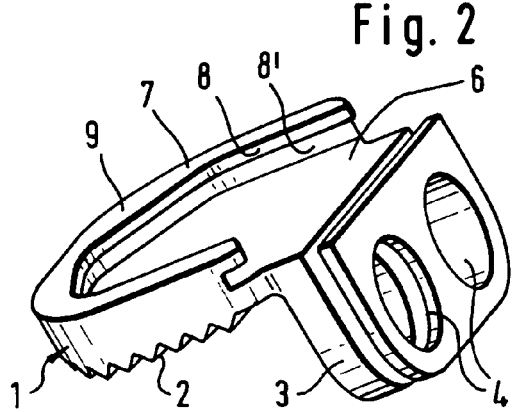
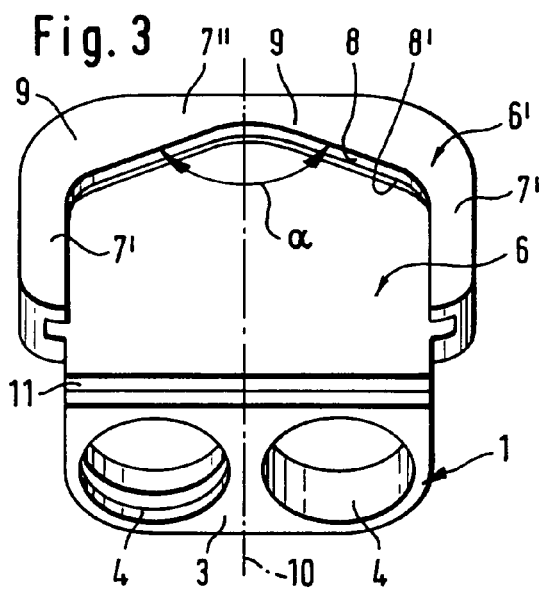
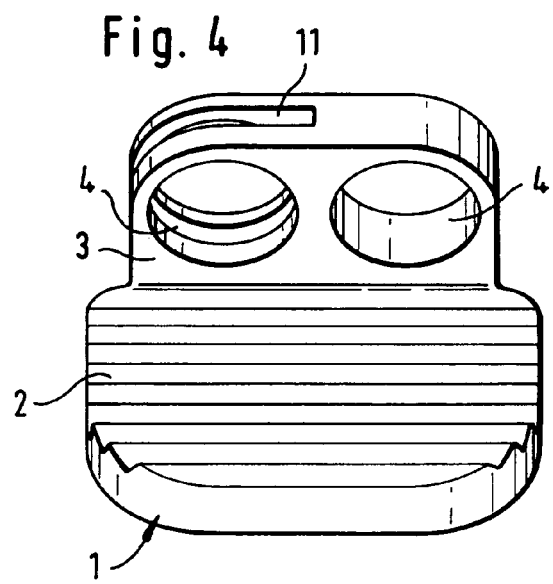
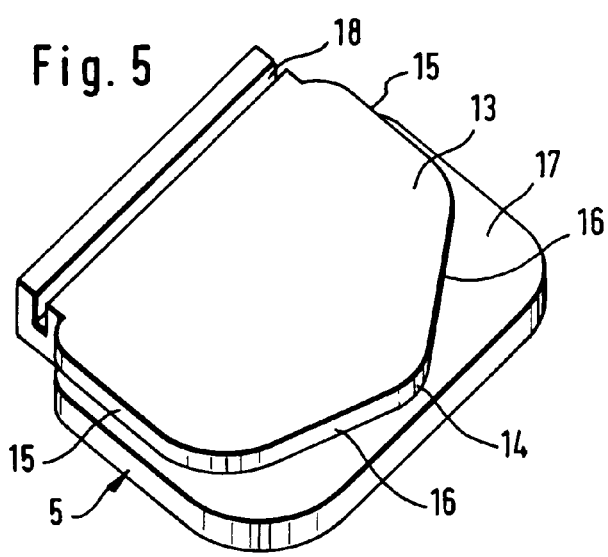
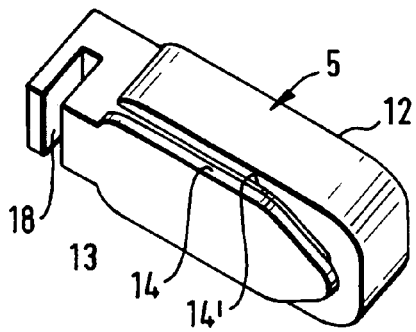

INTERVERTEBRAL DISC PROSTHESIS

FIELD AND BACKGROUND OF THE INVENTION

A known type of intervertebral disc prosthesis (WO 01/01893) has two metal cover plates and a polyethylene prosthesis core which forms a pair of slide surfaces with one of the two cover plates and is fixed on the other cover plate. For this fixing, the cover plate is provided with edge ridges whose undercut connection profile cooperates with a complementary connection profile on the underside of the prosthesis core. On the right and left lateral edges of the cover plate and of the prosthesis core, such connection profiles are provided parallel to one another. In addition, there is one such profile running in a straight line on the dorsal edge of the cover plate and of the prosthesis core. There is no such profile on the ventral edge, with the result that the prosthesis core can be pushed into the connection profiles of the cover plate from the ventral direction. The prosthesis core is secured in the assembled position by a pair of locking elements provided on the ventral edge. Although the connection profiles are produced almost free of play, an important concern in prosthesis production is to ensure that, even in the case of production tolerances, it is possible to rule out any movement of the prosthesis core relative to the cover plate holding it. In particular, rotation movements of the prosthesis core relative to the cover plate holding it must be ruled out. The invention has recognized that this can be improved not only by precision production but also by a special arrangement of the connection profiles.

SUMMARY OF THE INVENTION

According to the invention, provision is made that the connection profiles include at least one pair of connection profile sections which are symmetrical with respect to the AP direction and are arranged at an angle to one another. AP direction signifies the anteroposterior direction. The profile sections arranged at an angle to one another according to the invention create a triangular configuration which counteracts twisting of the prosthesis core relative to the cover plate if play exists between the connection profiles of the cover plate and of the prosthesis core. The connection profiles can basically be made up exclusively of such profile sections arranged at an angle to one another. However, these can also be provided additionally to connection profiles arranged in parallel on the lateral edges of the cover plate and of the prosthesis core. They are intended to run in a substantially straight line and are preferably arranged at least on the dorsal side. The angle between the profile sections arranged at an angle to one another should not be greater than 150°. The limit preferably lies for example at 140°.

BRIEF DESCRIPTION OF THE DRAWINGS

The invention is explained in more detail below with reference to the drawing which depicts an advantageous illustrative embodiment and in which:

FIG. 1 shows a perspective view of the end plate with the prosthesis core secured on it, FIGS. 2 to 4 show different views of the same end plate without prosthesis core, and FIGS. 5 and 6 show perspective views of the prosthesis core.

DETAILED DESCRIPTION OF THE INVENTION

The end plate 1, which is normally used as the lower end plate, has an approximately oval contour and comprises a toothed fastening surface 2 for bearing on the vertebral body and a flange 3 which comes to lie on the ventral side of the vertebral body and can be screwed to the latter via screw holes 4. On that side opposite the fastening surface 2, the one normally lying to the top, the cover plate 1 forms a support for the prosthesis core 5. This support consists of a plane surface 6 and, surrounding the latter, an edge 7 which is composed of two parallel sections 7' on the lateral sides of the plate and of a dorsal edge 7". The outer contour of the edge 7 corresponds to the oval contour of the cover plate. On its side facing toward the surface 6, the edge is provided with a profile ridge 8 and, below the latter, with an undercut 8'. The connection profile thereby formed on the inner side of the edge 7 runs in a straight line in the lateral sections 7 and 7' and parallel on both sides. In the dorsal section 7", the connection profile is composed of two sections 9. In each of these sections, the connection profile runs in a straight line. The profiles of both sections are arranged symmetrically with respect to the AP axis 10 of the implant and enclose an angle α which, in the example shown, is 140°.

The top of the edge 7 forms a plane surface 6' which runs parallel to the support surface 6 and likewise forms a support surface for the prosthesis core.

The flange 3 of the cover plate has a slit 11 which runs perpendicular to the connection profile 6 and whose function is explained later.

On its top 12, the prosthesis core 5 forms a slide surface which cooperates with the second cover plate (not shown) to form a hinge. The contour of the prosthesis core is identical to that of the cover plate 1. On its underside, it has a plane surface 13 which is intended to bear on the support surface 6 of the end plate 1 and has substantially the same contour shape. It is limited by a connection profile which is formed by a profile ridge 14 and an undercut 14'. This connection profile corresponds in a complementary manner to the connection profile 8, 9 of the edge ridge 7 of the cover plate 1. In particular, the connection profile is composed of two lateral sections 15 and two dorsal sections 16 which correspond respectively to the lateral and dorsal sections of the edge 7 of the cover plate 1 and can cooperate with these in a form-fitting manner.

Outside the connection profile 14, 14', on the underside of the prosthesis core 5 there is a plane surface 17 which corresponds to the support surface 6' on the top of the edge 7 of the cover plate 1 and cooperates with this when the prosthesis core is mounted on the cover plate 1.

The prosthesis is assembled by means of the prosthesis core being pushed with its connection profile 14, 14' into the corresponding connection profiles 8, 8' from the direction of the open ventral side. When the prosthesis core has been pushed in fully, its profile ridge 14 fits, not only in the area of the lateral sections 7' but also in the area of the dorsal section 7", into the undercut 8' of the edge 7 of the cover plate, the connection profiles lying on one another with substantially full-surface contact.

At the location where the slit 11 is situated in the gap 3, the prosthesis core has a groove 18 which is flush with the gap 11 when the prosthesis core has reached its end position in which the dorsal connection profiles abut one another. A plate (not shown) is pushed into the gap 11 and the groove 18 and secures the prosthesis core in this position relative to the cover plate 1. The plate is in turn secured by means of also having a bore at the location of the screw hole shown on the left in FIG. 3, through which bore a fastening screw extends.

By virtue of the fact that the connection profiles of the prosthesis core and of the cover plate are equipped, respectively, with the sections 9 and 16 which each form a triangle, it is possible, in comparison with known prostheses, to obtain increased stability of the position of the prosthesis core relative to the cover plate 1. In particular, its stability with respect to relative movements in the sense of rotation is thereby increased.

The invention claimed is:

1. An intervertebral disc prosthesis, comprising two cover plates and a prosthesis core, the prosthesis core being connected to one of the cover plates by complementary undercut connection profiles on the one cover plate and the prosthesis core, wherein the connection profile on the prosthesis core is disposed on a leading edge and two lateral edges relative to an implanted position of the prosthesis, the leading edge having a triangular configuration with a single tip projecting outward beyond the lateral edges, the leading edge comprising a pair of first profile sections being substantially straight and forming sides of the triangular configuration that meet at an angle not greater than 150°, the lateral edges comprising a pair of second profile sections parallel to one another and being arranged in an anteroposterior direction relative to the implanted position, and wherein the connection profile on the one cover plate has a triangular configuration with a single tip projecting outward beyond a pair of lateral edges parallel to one another.

2. The intervertebral disc prosthesis according to claim 1, wherein the prosthesis core is held in engagement with the one cover plate by an engaging structure arranged on a ventral side of the prosthesis core and the one cover plate relative to the implanted position.

* * * * *